(12) United States Patent
Cao et al.

(10) Patent No.: US 12,385,089 B2
(45) Date of Patent: Aug. 12, 2025

(54) METHODS FOR SINGLE-MOLECULE ANALYSIS

(71) Applicant: Bionano Genomics, Inc., Philadelphia, PA (US)

(72) Inventors: Han Cao, San Diego, CA (US); Ming H. Xiao, Huntingdon Valley, PA (US); Alex Hastie, San Diego, CA (US); Michael G. Saghbini, Poway, CA (US); Henry B. Sadowski, San Diego, CA (US)

(73) Assignee: BIONANO GENOMICS, INC., San Diego, CA (US)

( * ) Notice: Subject to any disclaimer, the term of this patent is extended or adjusted under 35 U.S.C. 154(b) by 0 days.

(21) Appl. No.: 14/765,537

(22) PCT Filed: Feb. 3, 2014

(86) PCT No.: PCT/US2014/014501
§ 371 (c)(1),
(2) Date: Aug. 3, 2015

(87) PCT Pub. No.: WO2014/123822
PCT Pub. Date: Aug. 14, 2014

(65) Prior Publication Data
US 2015/0368706 A1 Dec. 24, 2015

Related U.S. Application Data

(60) Provisional application No. 61/761,189, filed on Feb. 5, 2013.

(51) Int. Cl.
| *C12Q 1/6809* | (2018.01) |
| *C12Q 1/6806* | (2018.01) |
| *C12Q 1/6869* | (2018.01) |
| C07H 21/00 | (2006.01) |
| C12N 9/00 | (2006.01) |

(52) U.S. Cl.
CPC ......... *C12Q 1/6869* (2013.01); *C12Q 1/6806* (2013.01); *C12Q 1/6809* (2013.01)

(58) Field of Classification Search
CPC .................................................. C12Q 1/6809
USPC ....................................................... 435/6.1
See application file for complete search history.

(56) References Cited

U.S. PATENT DOCUMENTS

| 4,521,509 A * | 6/1985 | Benkovic ............... C07H 21/00 436/63 |
| 5,677,126 A * | 10/1997 | Bensimon ................ C12Q 1/68 422/504 |
| 5,736,334 A * | 4/1998 | Spies ..................... C12Q 1/706 435/5 |
| 7,771,944 B2 | 8/2010 | Xiao et al. |
| 7,816,079 B2 | 10/2010 | Fischer |
| 7,960,105 B2 * | 6/2011 | Schwartz .............. C12Q 1/6816 536/23.1 |
| 8,158,388 B2 * | 4/2012 | Evans ................... C12Q 1/6844 435/91.2 |
| 8,628,919 B2 * | 1/2014 | Xiao ...................... G16B 20/20 536/23.1 |
| 2002/0187508 A1 * | 12/2002 | Wong ................... C12Q 1/6825 435/5 |
| 2003/0100094 A1 * | 5/2003 | Heiter ..................... C12N 9/22 435/199 |
| 2003/0215924 A1 | 11/2003 | Barnes |
| 2005/0019784 A1 * | 1/2005 | Su ......................... C12Q 1/6869 435/6.12 |
| 2005/0053986 A1 * | 3/2005 | Makarov ............... C12Q 1/6855 435/6.1 |
| 2007/0148674 A1 | 6/2007 | Berres et al. |
| 2008/0199916 A1 | 8/2008 | Zheng et al. |
| 2008/0242556 A1 * | 10/2008 | Cao ....................... C12Q 1/6874 506/10 |
| 2009/0111115 A1 | 4/2009 | Drmanac et al. |
| 2009/0117551 A1 * | 5/2009 | Suzuki ............... G01N 21/6428 435/6.12 |
| 2009/0305273 A1 | 12/2009 | Cao et al. |
| 2010/0129879 A1 * | 5/2010 | Ach ....................... C12Q 1/6827 536/22.1 |
| 2010/0330556 A1 * | 12/2010 | Peter ..................... C12Q 1/6858 435/6.1 |
| 2010/0330557 A1 | 12/2010 | Yakhini et al. |
| 2011/0171634 A1 * | 7/2011 | Xiao ...................... G16B 20/20 530/391.1 |
| 2011/0201509 A1 * | 8/2011 | Tegenfeldt ........ B01L 3/502761 506/7 |
| 2011/0227558 A1 * | 9/2011 | Mannion .......... G01N 33/48721 257/253 |
| 2011/0296903 A1 | 12/2011 | Cao et al. |
| 2012/0237936 A1 * | 9/2012 | Xiao ....................... C12Q 1/683 435/6.11 |

(Continued)

FOREIGN PATENT DOCUMENTS

| JP | 2011-526787 | 10/2011 |
| WO | WO 2011/050147 | 4/2011 |

OTHER PUBLICATIONS

"Viruses" (Wikipedia.com, accessed Nov. 24, 2012).*
"How many species of bacteria are there" (wisegeek.com; accessed Jan. 21, 2014).*
"Fungi," (Wikipedia.com; accessed Jun. 3, 2013).*
"Plant," (Wikipedia.com; accessed Aug. 28, 2015).*
"Mammal," (Wikipedia.com; accessed Sep. 22, 2011).*
"Murinae," (Wikipedia.com, accessed Mar. 18, 2013).*
"Fish," (Wikipedia.com, accessed Nov. 2, 2014).*
"List of sequenced bacterial genomes" (Wikipedia.com; accessed Jan. 24, 2014).*

(Continued)

*Primary Examiner* — Bradley L. Sisson
(74) *Attorney, Agent, or Firm* — Dickinson Wright PLLC

(57) ABSTRACT

Methods for single-molecule preparation and analysis are disclosed herein. The methods can, for example, be used for isolating and analyzing DNA from various biological samples.

16 Claims, 8 Drawing Sheets

(56) References Cited

U.S. PATENT DOCUMENTS

| | | | | |
|---|---|---|---|---|
| 2012/0283145 | A1* | 11/2012 | Wang | C12Q 1/6806 |
| | | | | 506/26 |
| 2012/0301926 | A1* | 11/2012 | Chen | C12Q 1/6806 |
| | | | | 435/91.5 |
| 2012/0322058 | A1 | 12/2012 | Regan et al. | |
| 2013/0012399 | A1* | 1/2013 | Myers | C12Q 1/6869 |
| | | | | 506/2 |
| 2014/0221218 | A1 | 8/2014 | Cao et al. | |
| 2015/0368706 | A1 | 12/2015 | Cao et al. | |

OTHER PUBLICATIONS

Examination Report dated Feb. 21, 2019 for Australian Application No. 2014215586.
Office Action dated Feb. 14, 2018 for Chinese Application No. 201480007595.1 (with machine translation in English).
Office Action dated Jul. 26, 2019 for Chinese Application No. 201480007595.1 (with machine translation in English).
Office Action dated Jan. 23, 2018 for Japanese Application No. 2015-556985.
Office Action dated Jan. 22, 2019 for European Application No. 14748636.9.
U.S. Appl. No. 61/713,862, filed Oct. 15, 2012, Saghbini et al.
Advisory Action and Interview Summary dated May 11, 2017 in U.S. Appl. No. 14/171,369.
Baday et al., Multicolor super-resolution DNA imaging for genetic analysis. Nano Lett. Jul. 11, 2012 vol. 12 No. 7 pp. 3861-3866. Especially p. 3 para. 3-6, p. 11 fig 4A.
Blakesley et al., (2010) Effort required to finish shotgun-generated genome sequences differs significantly among vertebrates. BMC Genomics 11: 21.
Brenchley et al., (2012) Analysis of the bread wheat genome using whole-genome shotgun sequencing. Nature 491: 705-710.
Cassidy et al., (1991) Molecular Characterization of a Low-Molecular-Weight Glutenin Cdna Clone from Triticum-Durum. Theoretical and Applied Genetics 81: 653-660.
Chain et al., (2009) Genome Project Standards in a New Era of Sequencing. Science 326: 236-237.
Das et al., (2010) Single molecule linear analysis of DNA in nano-channel labeled with sequence specific fluorescent probes. Nucleic Acids Research 38: e 177.
Dvorak, J., (2009) Triticeae Genome Structure and Evolution. Genetics and Genomics of the Triticeae Springer Science.
Extended European Search Report dated Aug. 12, 2016 in Application No. 14748636.9.
Green E., (2001) Strategies for the systematic sequencing of complex genomes. Nat Rev Genet 2: 573-583.
Hernandez et al., (2012) Next-generation sequencing and syntenic integration of flow-sorted arms of wheat chromosome 4A exposes the chromosome structure and gene content. Plant J 69: 377-386.
Howden et al., (2010) Complete genome sequence of *Staphylococcus aureus* strain JKD6008, an ST239 clone of methicillin-resistant *Staphylococcus aureus* with intermediate-level vancomycin resistance. J Bacteriol 192: 5848-5849.
International Search Report and Written Opinion mailed Apr. 17, 2014 in PCT Application No. PCT/US14/14501.
Lam et al. (2012) Genome mapping on nanochannel arrays for structural variation analysis and sequence assembly. Nat Biotechnol 30: 771-776.
Lee et al., (2012) Next-generation sequencing technologies and fragment assembly algorithms. Methods Mol Biol 855: 155-174.
Leroy et al., (2012) TriAnnot: A Versatile and High Performance Pipeline for the Automated Annotation of Plant Genomes. Front Plant Sci 3: 5.
Li et al., (2004) Sequence composition, organization, and evolution of the core Triticeae genome. Plant J 40: 500-511.
Li et al., (2011) Structural variation in two human genomes mapped at single-nucleotide resolution by whole genome de novo assembly. Nat Biotechnol 29: 723-730.

Lin et al. (2012) AGORA: Assembly Guided by Optical Restriction Alignment. BMC Bioinformatics 13: 189.
Luo et al. (2003) High-throughput fingerprinting of bacterial artificial chromosomes using the snapshot labeling kit and sizing of restriction fragments by capillary electrophoresis. Genomics 82: 378-389.
McPherson, T., (2001) A physical map of the human genome. Nature 409: 934-941.
Molecular Probes. ChromaTide Labeled Nucleotides [online] May 2, 2011 [retrieved Mar. 26, 2014]. Available on the Internet: <URL: http://www.lifetechnologies.com/order/catalog/product/011401>. Especially p. 1 Figs 1 and 2, p. 2 Table 1. It is noted that this reference was retrieved from the internet, and may have been available in some form at an earlier point in time.
Mun et al. (2008) The first generation of a BAC-based physical map of *Brassica rapa*. BMC Genomics 9: 280.
Nagarajan et al., (2008) Scaffolding and validation of bacterial genome assemblies using optical restriction maps. Bioinformatics 24: 1229-1235.
New England Biolabs. Nicking Endonucleases: The Discovery and Engineering of Restriction Enzyme Variants [online] NEB Expressions Jul. 2006, vol. 1.2 [retrieved Mar. 26, 2014]. Available on the Internet: <URL: https://www.neb.com/tools-and-resources/feature-articles/nicking-endonucleases-the-discovery-and-engineering-of-restriction-enzyme-variants>. Especially p. 1 para. 4. It is noted that this reference was retrieved from the internet, and may have been available in some form at an earlier point in time.
Office Action dated Nov. 9, 2015 in U.S. Appl. No. 14/171,369.
Office Action dated Feb. 7, 2017 in U.S. Appl. No. 14/171,369.
Office Action dated Aug. 22, 2016 in Chinese Application No. 201480007595.1 (with machine translation).
Office Action dated May 17, 2017 in Chinese Application No. 201480007595.1 (with machine translation).
Office Action dated May 3, 2017 in European Application No. 14748636.9.
Paul et al., PCR incorporation of modified dNTPs: the substrate properties of biotinylated dNTPs. Biotechniques Apr. 2010 vol. 48 No. 4 pp. 333-334. Especially p. 333 col. 1 para. 2 and col. 2 para 3.
Paux et al., (2008) A Physical Map of the 1-Gigabase Bread Wheat Chromosome 3B. Science 322: 101-104.
Philippe et al., (2012) Whole Genome Profiling provides a robust framework for physical mapping and sequencing in the highly complex and repetitive wheat genome. BMC Genomics 13: 47.
Project IRGS (2005) The map-based sequence of the rice genome. Nature 436: 793-800.
Riley et al., (2011) Optically mapping multiple bacterial genomes simultaneously in a single run. PLoS One 6: e27085.
Schnable et al., (2009) The B73 maize genome: complexity, diversity, and dynamics. Science 326: 1112-1115.
Schwartz et al. (1993) Ordered restriction maps of *Saccharomyces cerevisiae* chromosomes constructed by optical mapping. Science 262: 110-114.
Sheth et al., "Optimizations of Physical Genome Map Contiguity by In Silico Ligation", XP002760296, Retrieved from the Internet: URL: http://bionanogenomics.com/wp-content/uploads/2016/01/PSheth_BioNano_PAG_2016_P1272.pdf, [retrieved on Jul. 27, 2016], Jan. 2016. This reference also lists a copyright date of 2015. It is noted that this reference was retrieved from the internet, and may have been available in some form at an earlier point in time.
Smith et al., (1975) Characterisation of the wheat genome by renaturation kinetics. Chromosoma 50: 223-242.
Soderlund et al., (1997) FPC: a system for building contigs from restriction fingerprinted clones. Comput Appl Biosci 13: 523-535.
Teague et al. (2010) High-resolution human genome structure by single-molecule analysis. Proc Natl Acad Sci USA 107: 10848-10853.
The *Arabidposis* Genome Initiative, 2000, Analysis of the genome sequence of the flowering plant *Arabidopsis thaliana*. Nature 408:796-815.
Van Oeveren et al., (2011) Sequence-based physical mapping of complex genomes by whole genome profiling. Genome Research 21(4): 618-625.

(56) References Cited

OTHER PUBLICATIONS

Venter et al., (2001) The Sequence of the Human Genome. Science 291: 1304-1351.

Warren et al., (2006) Physical map-assisted whole-genome shotgun sequence assemblies. Genome Res 16: 768-775.

Xiao et al., Rapid DNA mapping by fluorescent single molecule detection. Nucleic Acids Research, ePub Dec. 14, 2006 vol. 35 No. 3 pp. e16 1-e16 12. Especially p. 1 col. 2 para. 3, p. 3 fig. 2, p. 3 col. 1 para. 1.

Zhou et al., (2007) Validation of rice genome sequence by optical mapping. BMC Genomics 8: 278.

Zhou et al., (2009) A single molecule scaffold for the maize genome. PLoS Genet 5: e1000711.

Zuccolo et al., (2007) Transposable element distribution, abundance and role in genome size variation in the genus *Oryza*. BMC Evolutionary Biology 7: 152.

Examination Report dated Feb. 20, 2020 in Australian Patent Application No. 2014215586.

Office Action dated Dec. 19, 2019 in Canadian Patent Application No. 2,900,054.

Summons to Attend Oral Proceedings dated Oct. 28, 2019 in European Patent Application No. 14748636.9.

Office Action dated Oct. 30, 2020 in Canadian Patent Application No. 2,900,054.

Office Action dated Apr. 9, 2021 in Chinese Application No. 201480007595.1 (with machine translation in English).

Office Action dated May 17, 2021 in Australian Patent Application No. 2020201280.

Office Action dated Aug. 26, 2021 in Chinese Application No. 201480007595.1 (with machine translation in English).

Office Action dated Oct. 14, 2021 in Canadian Patent Application No. 2,900,054.

* cited by examiner

FIG. 1

A:

B:

ARROWHEADS REPRESENT NICK LOCATION AND THE DIRECTION OF TRANSLATION XXXXX REPRESENTS THE NEWLY SYNTHESIZED STRANG.

FIG. 2

| E. coli DNA | CENTER OF MASS | MAPPING TO REFERENCE GENOME | FALSE POSITIVE | FALSE NEGATIVE |
|---|---|---|---|---|
| NICK-LABEL - NO REPAIR | 116.3 Kb | 86.5% | 8.3% | 11.1% |
| NICK-LABEL - PRECR REPAIR | 168.3 Kb | 89.2% | 8.3% | 10.5% |
| NICK-LABEL PRECR CHOCKED REPAIR NO DGTP | 193.5 Kb | 89.2% | 8.7% | 10.2% |
| NICK-LABEL PRECR CHOCKED REPAIR NO DATP AND DGTP | 180.2 Kb | 91.5% | 9.1% | 11% |
| NICK-LABEL TAQ CHOCKED REPAIR NO DGTP | 235 Kb | 87.2% | 8.3% | 13% |

FIG. 3

| E. coli DNA | CENTER OF MASS | MAPPING TO REFERENCE GENOME | FALSE POSITIVE | FALSE NEGATIVE |
|---|---|---|---|---|
| NICK-LABELING - NO REPAIR | 143 Kb | 85.2% | 14.1% | 12.2% |
| NICK-LABELING FENL - ECOLI LIGASE REPAIR | 201.9 Kb | 81.5% | 12% | 10.6% |

FIG. 4

| Drosophilia DNA | CENTER OF MASS | MAPPING TO REFERENCE GENOME | LABELS PER 100 KB | FALSE POSITIVE | FALSE NEGATIVE |
|---|---|---|---|---|---|
| NICK-LABEL PRECR REPAIR BBVCI | 165.8 Kb | 51.8% | 6.8 | 11.6% | 10% |
| NICK-LABEL PRECR REPAIR BSPQI | 187.6 Kb | 52.6% | 10 | 11.5% | 10.8% |

METHODS FOR SINGLE-MOLECULE ANALYSIS

CROSS-REFERENCE TO RELATED APPLICATIONS

The present Application is the National Phase of PCT Application No. PCT/US2014/014501, filed Feb. 3, 2014. The present Application claims the benefit of U.S. Provisional Application No. 61/761,189 filed Feb. 5, 2013, which is hereby incorporated by reference in its entirety.

BACKGROUND

Technical Field

The present invention relates to the field of nanotechnology and to the field of single molecule genomic analysis.

Description of the Related Art

Next-generation sequencing (NGS) technologies have enabled high-throughput and low-cost generation of sequence data. However, de novo genome assembly remains a great challenge, particularly for large genomes. NGS short reads are often insufficient to create large contigs that span repeat sequences and facilitate unambiguous assembly. Plant genomes are notorious for containing high quantities of repetitive elements, which combined with huge genome sizes, makes accurate assembly of these large and complex genomes intractable.

Accurate de novo assembly of sequence reads represents the weak link in genome projects despite advances in high-throughput sequencing [1,2]. There are two general steps in genome sequence assembly, generation of sequence contigs and scaffolds, and their anchoring on genome-wide, lower resolution maps. NGS platforms generate sequence reads ranging from 25 to more than 500 bases [3], while reads of up to 1000 bases can be obtained by Sanger sequencing with high accuracy. NGS reads are often too short for unambiguous assembly. Paired-end reads can bridge contigs into scaffolds, but there are often gaps within the scaffolds. To order contigs and scaffolds, high-resolution genomic maps from an independent technology platform are needed. They may be of chromosomal scale, i.e., genetic maps, or regional scale, i.e., contigs of bacterial artificial chromosomes (BACs) or fosmids [4]. Contigs and scaffolds may be difficult to map if they are too short compared to the map resolution. For example, maps may have a resolution of 50-150 kb, while many contigs and scaffolds may only span a few kilobases. Additionally, there are errors in the contigs and scaffolds themselves, often due to misassembly of repeat sequences. Typical medium to large genomes contain 40-85% repetitive sequences [5-8], dramatically hindering effective de novo sequence assembly.

Genome finishing has relied on guidance of a physical map for large and complex genomes, including human, arabidopsis [9], rice [10] and maize [11,12]. BAC-based restriction fragment physical mapping of complex genomes is fairly robust because even in the presence of interspersed repeat sequences along the BAC inserts (typically 100-220 kb long), a unique pattern of restriction fragments is generated. State of the art technologies for physical map construction include SNaPshot [13,14], whole-genome profiling [15,16], optical mapping [17,18], and genome mapping [19]. SNaPshot is a restriction fingerprinting method which uses one or more restriction enzymes and fluorescent labels followed by separation of fragments by capillary electrophoresis. SNaPshot has been used for physical mapping of wheat and other genomes [14,20]. Optical mapping provides an additional layer of information by retaining the physical order of restriction sites along DNA molecules immobilized on a surface [18]. It has been applied to the maize and the rice genome [11,21]. One can validate a sequence assembly by comparing in silico sequence motif maps to consensus optical maps [22-25]. However, information density for optical maps is only about one site per 20 kb, and the technology is limited in utility by high error-rates, non-uniform DNA linearization, and low throughput. Therefore, a high-resolution (e.g., <5 kb) DNA sequencing-independent mapping method that can overcome these constraints of optical mapping is much needed.

SUMMARY

According to some embodiments, a method of characterizing a DNA is provided. The method can comprise nicking a first DNA at a first sequence motif, in which the first DNA is double stranded, and in which the first DNA remains double-stranded adjacent to the nicks. The method can comprise labeling the nicks on the first DNA with a first label. The method can comprise linearizing the first DNA. The method can comprise detecting the pattern of the first label on the linearized first DNA. In some embodiments, the first DNA is linearized after labeling. In some embodiments, the method further comprises marking the first DNA with a third label, in which the third label is non-sequence-specific, and in which the third label is different from the first label. In some embodiments, the method further comprises repairing at least some of the nicks on the first DNA. In some embodiments, the nicks on the first DNA are repaired prior to marking the labeled first DNA with the third label. In some embodiments, the method further comprises nicking a second DNA at the first sequence motif, labeling the nicks on the second DNA with the first label, linearizing the second DNA; and detecting the pattern of the first label on the linearized second DNA. In some embodiments, the method further comprises marking the second DNA with the third label. In some embodiments, the method further comprises repairing at least some of the nicks on the second DNA. In some embodiments, the nicks on the second DNA are repaired prior to marking the labeled second DNA with the third label. In some embodiments, the method further comprises nicking the first DNA at a second sequence motif, in which the repaired first DNA remains double-stranded adjacent to the nick, and labeling the nicks at the second sequence motif on the first DNA with a second label, in which the second label is different from the third label. In some embodiments, the method further comprises repairing the nicks on the first DNA following labeling with the second label. In some embodiments, the nicks on the first DNA are repaired prior to marking the first DNA with the third label. In some embodiments, the method further comprises detecting the pattern of the second label on the first DNA. In some embodiments, the method further comprises nicking the second DNA at a second sequence motif, in which the second DNA remains double-stranded adjacent to the nicks; and labeling the nicks at the second sequence motif on the second DNA with a second label, wherein the third label, if used, is different from the second label. In some embodiments, the second DNA is nicked at the second sequence motif after any nicking at the first motif is repaired. In some embodiments, the method further comprises repairing the nicks on the second DNA following labeling with the second label. In some embodiments, the method further comprises detecting the pattern of the second label on the second DNA.

According to some embodiments, a method of characterizing DNA is provided. The method can comprise nicking one strand of a first DNA at a recognition sequence with a first nicking endonuclease, in which the first DNA is double stranded, and in which the first DNA remains double-stranded adjacent to the nicks. The method can comprise labeling the first DNA at the nicking sites with a first label. The method can comprise repairing the nicks on the first DNA. The method can comprise nicking a complementary strand of a second DNA at the recognition sequence with a second nicking endonuclease, in which the complementary strand of the second DNA is complementary to the one strand of the first DNA, in which the second DNA is double stranded, and in which the second DNA remains double-stranded adjacent to the nicks. The method can comprise labeling the second DNA at the nicking sites with a second label. The method can comprise repairing the nicks on the second DNA. The method can comprise linearizing the marked first DNA and marked second DNA. The method can comprise detecting a pattern of the first and second label on the linearized first DNA and linearized second DNA. In some embodiments, the method further comprises marking the repaired first and second DNA with a third label, in which the third label is non-sequence specific. In some embodiments, the first DNA and the second DNA are both from a same source. In some embodiments, the first DNA and the second DNA are each from a different source. In some embodiments, the first and second label each comprise the same label. In some embodiments, the first and second label each comprise a different label. In some embodiments, the method further comprises comparing the pattern of label on the first DNA to the pattern of label on the second DNA. In some embodiments, the method further comprises assembling the labeled first DNA using the pattern of labeled motifs to construct a first DNA map. In some embodiments, the method further comprises assembling the labeled second DNA using the pattern of labeled motifs to construct a second DNA map. In some embodiments, the method further comprises assembling a plurality of first DNAs using overlap of the labeled sequence motifs to construct a first DNA map. In some embodiments, the method further comprises assembling a plurality of second DNAs using overlap of the labeled sequence motifs to construct a second DNA map, and comparing the first DNA map to the second DNA map. In some embodiments, the method further comprises nicking one strand of a third DNA at a recognition sequence with the first nicking endonuclease, thus generating at least one nicking site, in which the third DNA is double stranded, and in which the third DNA remains double-stranded adjacent to the nicks. The method can further comprise labeling the third DNA at the nicking sites. The method can further comprise nicking a complementary strand of a fourth DNA at the recognition sequence with the second nicking endonuclease, thereby generating at least one nicking site, wherein the complementary strand of the fourth DNA is complementary to the one strand of the third DNA. The method can further comprise labeling the fourth DNA at the nicking sites. The method can further comprise marking the repaired third and fourth DNAs with a third label, in which the third label is non-sequence-specific. In some embodiments, the method further comprises repairing the nicks on the third DNA and repairing the nicks on the fourth DNA. In some embodiments, the third DNA and fourth DNA are both from a same second source. In some embodiments, the method further comprises the third DNA comprises a first sample from the second source, and wherein the fourth DNA comprises a second sample from the second source. In some embodiments, the second source is different from the first source.

In some embodiments, any of the methods described herein further comprises comparing the pattern of the first label on the first DNA to a pattern of labels on a reference DNA. In some embodiments, any of the methods described herein further comprises comparing the pattern of the first labels to a pattern of labels on a reference DNA. In some embodiments, a method as described herein herein further comprises comparing the pattern of the first labels to a pattern of second labels on a reference DNA. In some embodiments, a method as described herein further comprises comparing the pattern of at least one of the first and second labels on the first DNA to a pattern of labels on a reference DNA. In some embodiments, a of the methods as described herein further comprises comparing the pattern of each of the first and second labels on the first DNA to a pattern of labels on a reference DNA.

In some embodiments herein, linearizing includes transporting the DNA into a nanochannel. In some embodiments herein, the third label comprises a non-sequence-specific label. In some embodiments herein, the first and second labels are independently selected from the group consisting of a fluorophore, a quantum dot, a dendrimer, a nanowire, a bead, a hapten, a streptavidin, an avidin, a neutravidin, a biotin, and a reactive group. In some embodiments herein, the first and second labels are independently selected from the group consisting of a fluorophore or a quantum dot. In some embodiments herein, at least one of the first and second labels comprises a non-optical label. In some embodiments herein, the labeling is carried out with a polymerase. In some embodiments herein, the labeling is carried out with a polymerase in the presence of dNTPs comprising the label. In some embodiments herein, the polymerase has a 5' to 3' exonuclease activity. In some embodiments herein, the polymerase leaves a flap region, and wherein the flap region is removed to restore a ligatable nick prior to the repairing with a ligase. In some embodiments herein, the flap region is removed using the 5' to 3' exonuclease activity of a polymerase under conditions wherein at least one nucleotide is present in limited concentration. In some embodiments herein, the flap region is removed using the 5' to 3' exonuclease activity of a polymerase under conditions wherein at least one nucleotide is omitted from the reaction. In some embodiments herein, the flap region is removed with a flap endonuclease. In some embodiments herein, the labeling is carried out with a polymerase in the presence of at least one species of dNTP. In some embodiments herein, the at least one species of dNTP is a single species of dNTP. In some embodiments herein, a method as described herein further comprises modulating activity of the polymerase by adjusting the temperature, dNTP concentration, cofactor concentration, buffer concentration, or any combination thereof, during labeling. In some embodiments herein, nicking the first motif or the second motif comprising nicking with Nt.BspQI.

According to some embodiments, a method of characterizing a DNA comprising a double-stranded DNA comprising at least one base flap on either strand of the DNA is provided. The method can comprise treating the double-stranded DNA with a 5' to 3' exonuclease activity of a polymerase under conditions in which at least one species of dNTP is present in limited concentration or omitted compared to other dNTPs that are present. The method can comprise ligating the nicks to restore strand integrity at flap regions. The method can comprise characterizing the DNA. In some embodiments, the label comprises a fluorophore or a quantum dot. In some embodiments, the label comprises a tag and wherein the tag is labeled with a fluorophore or a quantum dot.

According to some embodiments, a method of characterizing a DNA is provided. The method can comprise nicking a DNA at a first sequence motif, in which the DNA is double stranded, and in which the DNA remains double-stranded adjacent to the nicks. The method can comprise labeling the nicks on the DNA with a nucleotide comprising a first label such that one nucleotide is incorporated per nick site, in which the nucleotide further comprises a terminator, and in which the terminator is reversible. The method can comprise reversing the terminator. The method can comprise repairing the nicks. The method can comprise marking the repaired DNA with a second label, in which the second label is non-sequence-specific, and in which the second label is different from the first label. The method can comprise linearizing the DNA following labeling with the first and second labels. The method can comprise detecting the pattern of the first label on the linearized DNA. In some embodiments, at least one of the first or second label comprises a fluorophore or a quantum dot. In some embodiments, at least one of the first or second label comprises a tag, and the tag is labeled with a fluorophore or a quantum dot. In some embodiments, the label comprises a non-optical label.

BRIEF DESCRIPTION OF THE DRAWINGS

FIG. 1 shows fragmentations that can occur at fragile sites as a result of nicking, where nicks are closer to one another (FIG. 1A) or farther apart (FIG. 1B).

FIG. 2 shows DNA length corresponding to the midpoint in a size histogram showing molecules arranged from smallest to largest in length (or mass), (shown as "center of mass") the percent of DNA molecules that are mapped against a reference genome (shown as "mapping to reference genome"), and the false positive and false negative rates for mapping to a sequenced reference genome compared to a simulation for the same (shown as "false positive" and "false negative") rates in *E. coli* subjected to the following treatments: 1.) no repair, 2.) repair with PreCR as recommended by manufacture (New England BioLabs), 3.) repair with PreCR under conditions of omitting dGTP, 4.) repair with PreCR under conditions of omitting dATP and dGTP, and 5.) repair with Taq polymerase under conditions of omitting dGTP.

FIG. 3 shows center of mass, percent mapping to a reference genome, and false positive and false negative rates in *E. coli* subjected to the following treatments: 1.) no repair, or 2) treatment with FEN I to remove flaps followed by a ligase to repair the translated nicks.

FIG. 4 shows center of mass, percent mapping to a reference genome, and false positive and false negative rates in Drosophila subjected to the following treatments: 1.) nicking with Nt.BspQI and PreCR repair, and 2.) nicking with Nb.BbVCI and PreCR repair.

DETAILED DESCRIPTION

Figure 5A:
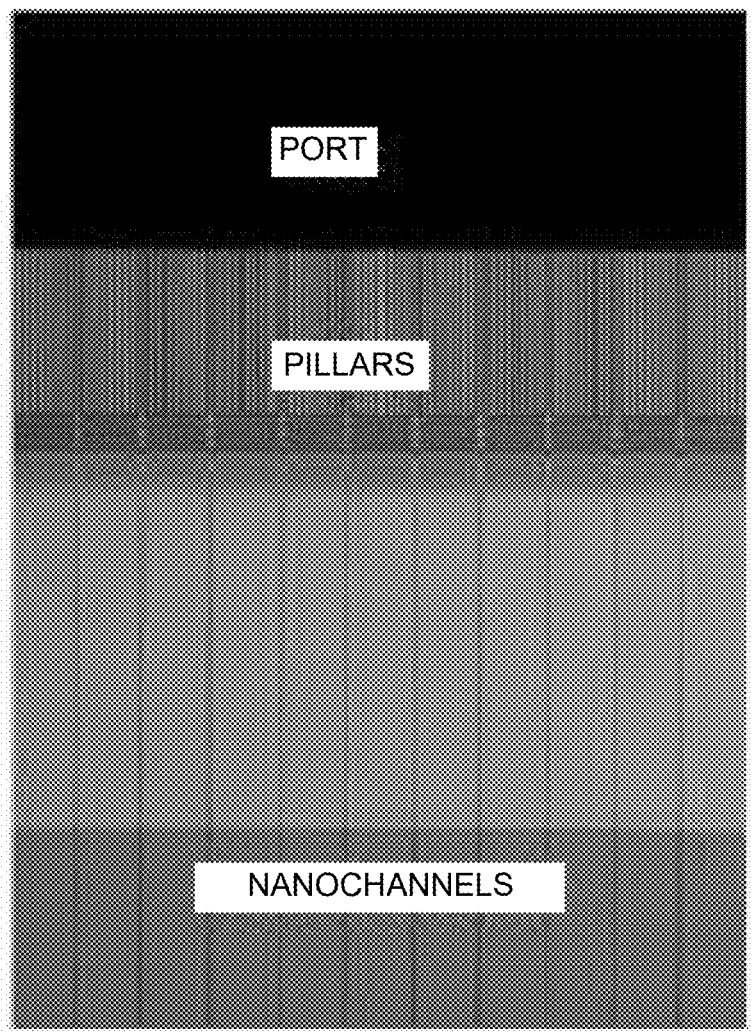
FIGS. 5A-5F show two-color genome mapping with two enzymes, including the layout of an IrysChip (FIG. 5A), linearization in nanochannels (FIG. 5B), distribution of labels at sequence-specific locations (FIG. 5C), the alignment of consensus maps (FIG. 5D), and a map of a genomic region based on overlaps of consensus maps (FIGS. 5E-F) as described in Example 4.

Maintaining and restoring the integrity of DNA strands is essential for obtaining long labeled molecules that are useful for complex genome mapping and information density. The methods described herein provide approaches to minimize the formation of fragile DNA sites and fragmentation of DNA, restore the structural integrity of DNA following the use of nicking approaches, and maximize the information content of DNA in order to generate high-resolution maps.

Described herein are approaches that can be used in conjunction with a nanochannel array to reproducibly and uniformly linearize DNA. In addition to improved noise characteristics (e.g., by virtue of keeping DNA in solution rather than affixed), these approaches can entail cycles of channel-loading and imaging to generate high-throughput DNA reads. Genome mapping on nanochannel arrays at the single-molecule level overcomes many of the limitations of preexisting technologies and is described in depth in Lam E T et al. (Genome mapping on nanochannel arrays for structural variation analysis and sequence assembly, *Nat Biotechnol* 30: 771-776, 2012), which is hereby incorporated by reference in its entirety. In some embodiments described herein, a genome mapping approach allows multiple motifs to be labeled with different colors is employed, significantly increasing information density.

In some embodiments, a high-resolution physical map is constructed. The physical map can be used to validate or correct a physical map generated using another method, such as SNaPshot fingerprinting technology. In some embodiments, the physical map is used to validate assembled regions and correct inaccuracies in sequence scaffolds. The physical map can also be used to facilitate de novo sequence assembly of a region by anchoring sequence scaffolds. In some embodiments, the physical map is used to produce a highly accurate and complete sequence assembly.

In some embodiments provided herein, nick labeling is used to prepare DNA for analysis. As part of the nick labeling process, nicks can move closer to one another (as shown in FIG. 1A) or farther apart (as shown in FIG. 1B). Without being limited by any one theory, it has been discovered that fragile sites occur when two nicks are <1 Kb apart on opposite DNA strands. Fragmentation can occur at fragile sites due, for example, to: 1) mechanical manipulation, 2) heat required for labeling, 3) strand extension associated with labeling and certain kinds of repair (e.g., using the exonuclease activity of polymerases), or 4) shear forces associated with linearizing DNA molecules. In general, the shorter the distance between nicks, the more frequent the fragmentation, particularly if labeling decreases the original distance (FIG. 1A). As described herein, it has been found that repairing nicks can ameliorate the breakage of DNA. As such, in some embodiments, a DNA is repaired after nicking. However, it is also contemplated herein that under some circumstances, a nicked and labeled DNA can be analyzed without nick repair, for example if nicks occur at very low frequency such that there is only a low likelihood of generating fragile sites. As such, in some embodiments, a DNA is not repaired after nicking, or is not repaired after nicking and labeling.

In some embodiments, the methods described herein utilize nicking enzymes to create sequence-specific nicks that are subsequently labeled, for example by a fluorescent nucleotide analog. In some embodiments, the nick-labeled DNA is stained with the intercalating dye, loaded onto a nanofluidic chip by an electric field, and imaged. In some embodiments, the DNA is linearized by confinement in a nanochannel array, resulting in uniform linearization and allowing precise and accurate measurement of the distance between nick-labels on DNA molecules comprising a signature pattern. In some embodiments, DNA loading and imaging can be repeated in an automated fashion. In some embodiments, a second nicking enzyme is used. In some embodiments, this second nicking enzyme is used with a second label color. Exemplary nickases that can be used in accordance with embodiments herein include, but are not limited to Nb.BbvCI; Nb.BsmI; Nb.BsrDI; Nb.BtsI; Nt.AlwI; Nt.BbvCI; Nt.BspQI; Nt.BstNBI; Nt.CviPII and combinations thereof. In some embodiments, breaks or nicks are produced by physical or chemical processes, for example exposure to electromagnetic radiation (e.g., UV light), one or more free radicals, and the like.

In some embodiments, methods are provided to mitigate fragile site-based fragmentation. In some embodiments, reduced driving conditions are used to limit the rate of incorporation of a label, and therefore minimize fragmentation at the fragile sites. In some embodiments, reduced driving conditions are used to minimize shearing stress forces associated with DNA elongation. In some embodiments, drive is reduced by lowering the concentration of dNTPs, lowering reaction temperature, lowering cofactor concentration, adjusting buffer and salt concentration, or a combination thereof. Drive can be also be reduced at the level of repair by stimulating the exonuclease activity of a polymerase with a high concentration of dNTPs, then limiting extension by restricting or omitting at least one nucleotide (which can be referred to as "choked repair"). In a preferred embodiment, a single species of dNTP (e.g., dATP) is incorporated at the nick site, the flap is removed with a flap nuclease without extension, and ligation is performed.

In some embodiments, a suboptimal temperature for a thermophilic polymerase is used to reduce driving conditions. In some embodiments, the reaction temperature is about 35° C. to about 75° C., such as 35° C., 36° C., 37° C., 38° C., 39° C., 40° C., 41° C., 42° C., 43° C., 44° C., 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., or 75° C. In preferred embodiments, the temperature is between about 50° C. and about 55° C., between about 55° C. and about 60° C., between about 60° C. and about 65° C., or between about 50° C. and about 65° C.

In some embodiments, the polymerase used herein is thermostable. In some embodiments, the polymerase is mesophilic. In some preferred embodiments, the polymerase does not have a proofreading capability. In some preferred embodiments, the polymerase has a strand displacement capability. In some preferred embodiments, the polymerase has a 5' to 3' exonuclease activity. In some preferred embodiments, the polymerase does not have proofreading ability, but does have a strand-displacement capability and a 5' to 3' exonuclease activity.

Without being limited by any one theory, it has been discovered that during nick translation labeling, nicks that are close together on opposite strands will either move toward each other ("type A" destabilizing effect leading to fragmentation) or away from each other ("type B" stabilizing effect as the distance between nicks increases). In some embodiments a type A" effect is converted to a type B" effect by separately nick labeling a top strand and nick labeling a bottom strand of corresponding DNAs from the same source. In some embodiments, fragmentation at fragile sites is minimized by nick top labeling and nick bottom labeling different DNAs from the same source. For example, a first aliquot of DNA from a source can be nick labeled on the top stand, and a second aliquot of DNA from the same source can be nick labeled on the bottom strand. In some embodiments, nickases that target the same sequence motif but nick at opposite strands are used to target specific DNA strands to minimize the formation of fragile sites. In some embodiments, nickases have been modified to only bind to one strand of a double-stranded DNA. In some embodiments, nickases are used to target a single strand from a first DNA molecule, and a single strand from a second DNA molecule. In some of these embodiments, a single strand from the first DNA is targeted by a first nickase, and the complementary strand from the second DNA molecule is targeted with a second nickase that recognizes the same sequence motif as the first nickase. In some embodiments, the orientation of extension is reversed for one of the strands. For example, in some embodiments, extension from the site of nicking occurs in one direction for a first DNA molecule, and in the opposite direction for a second DNA molecule. In some embodiments, extension from the site of nicking occurs in one direction for a top strand of a DNA molecule, and in the opposite direction for the bottom strand for the same DNA molecule.

In some embodiments, a reference map is used for assembly as described herein.

In some embodiments, a plurality of nickases are used to maximize information density. In some embodiments, molecules nicked by the plurality of nickases are assembled using a reference map.

In some embodiments, more than one nicking step is used to maximize information density. In some embodiments, the molecule or molecules subjected to more than one nicking step are assembled using a reference map.

In some embodiments, DNA is linearized. Means of linearizing DNA can include the use of shear force of liquid flow, capillary flow, convective flow, an electrical field, a dielectrical field, a thermal gradient, a magnetic field, combinations thereof (e.g., the use of physical confinement and an electrical field), or any other method known to one of skill in the art. In some embodiments, the channel(s) described herein have a cross sectional dimension in the micrometer range. In some preferred embodiments, channels have a cross sectional dimension in the nanometer range. Examples of nanochannels and methods incorporating the use of nanochannels are provided in U.S. Publication Nos. 2011/0171634 and 2012/0237936, which are hereby incorporated by reference in their entireties.

In some embodiments, a second motif is investigated in a molecule of interest. In some embodiments, the second motif includes at least one binding site for a binding entity selected from a non-cutting restriction enzyme, a zinc finger protein, an antibody, a transcription factor, a transcription activator like domain, a DNA binding protein, a polyamide, a triple helix forming oligonucleotide, and a peptide nucleic acid. In some embodiments, marking or tagging of the second motif is effected with a binding entity comprising a second label. In some embodiments, marking is performed with a label that does not cut or nick the DNA. In some embodiments, tagging is performed with a label that does not cut or nick the DNA.

In some preferred embodiments, the second motif includes at least one binding site for a peptide nucleic acid. In some embodiments, tagging is effected with a peptide nucleic acid comprising a second label. In other embodiments, the second motif includes at least one recognition sequence for a methyltransferase. In some embodiments, tagging is performed with a methyltransferase. In some embodiments, tagging is performed with a methyltransferase comprising a modified cofactor which includes a second label.

In some embodiments, a modified cofactor is used. In some embodiments, the modified cofactor contains a second label that functions as a transferable tag which becomes covalently coupled to a methyltransferase recognition sequence. In other embodiments, the modified cofactor contains a second label that is directly coupled to a methyltransferase recognition sequence.

In some embodiments, the labels described herein are selected from a fluorophore, a quantum dot, a dendrimer, a nanowire, a bead, a hapten, a streptavidin, an avidin, a neutravidin, a biotin, or a reactive group. In some preferred embodiments, the first and second labels described herein are selected from a fluorophore or a quantum dot.

In some embodiments, at least one label as described herein comprises a non-optical label. A variety of non-optical labels can be used in conjunction with embodiments herein. In some embodiments a non-optical label comprises an electronic label. Exemplary electronic labels include, but are not limited to molecule with a strong electric charge, for example ions such as a metal ions, charged amino acid side chain, or other cations or anions. An electronic label can be detected, for example, by conductivity (or resistivity) when the label is disposed in a detector. In some embodiments, a nanochannel comprises an electrode configured to determine the presence or absence of an electronic label by determining the conductivity or resistivity of a substance disposed in the channel. In some embodiments, the non-optical label comprises a metal, metal oxide (for example metal oxide), or silicon oxide moiety. In some embodiments, the non-optical label comprises a moiety (for example a nanoparticle) comprising a metal, metal oxide, or other oxide. The presence of a particular metal or oxide moiety can be detected, for example by nuclear magnetic resonance. In some embodiments, the label is configured to release a moiety, for example a proton or an anion, upon a certain condition (e.g. change of pH) and the presence or absence of released moiety is detected.

In some embodiments, two or more labels are the same. For example, if a first DNA is labeled and characterized, and a second DNA is labeled and characterized, the first DNA and second DNA can be labeled with the same type of label, for example the same fluorophore, same quantum dot, or same non-optical label. By way of example, the first DNA can be characterized in a first nanochannel, and the second DNA can be characterized in a second nanochannel, so the labeling patterns of the two DNAs can be distinguished, even if each DNA is labeled with the same labeling moiety. In some embodiments, the first label and second label are different, for example, if a single DNA is labeled at two or more different motifs.

Nucleotides with reversible terminators can form a first phosphodiester linkage, but prior to reversal of termination, cannot form (or have limited capacity to form) a second phosphodiester linkage. Thus, a nucleotide with a reversible terminator can be incorporated into a polynucleotide (for example at a nick site), but the nucleotide cannot form downstream phosphodiester linkages until the terminator is reversed. Reversal can be performed using techniques known to one skilled in the art. For example, the terminator can be attached to the nucleotide via cleavable linker, which can be cleaved, for example, via electromagnetic radiation. If nick repair is performed using labeled nucleotides comprising a 3' reversible terminator, a single labeled nucleotide can be incorporated into the nick, but the terminator can prevent additional labeled nucleotides from being incorporated into the nick. Accordingly, nick labeling can be limited to one labeled nucleotide per nick. Limiting nick labeling to one label moiety per nick can minimize potential bias from multiple labels being incorporated into the same nick. For example, if approaches are taken to limit labeling to one label moiety per nick, two nicks that are very close together can be resolved based on a relatively strong signal from the label (i.e. the possibility that two labels simply got incorporated into the same nick can be ruled-out). For example, if quantitative estimates of the number of nicks is desired, a one-label-per-nick approach can facilitate direct correlation between strength of label signal and the number of nicks. The label on the nucleotide comprising a reversible terminator can be as described herein. In some embodiments, the nucleotide comprising a reversible terminator comprises a quantum dot. In some embodiments, the nucleotide comprising a reversible terminator comprises a fluorophore. In some embodiments, the nucleotide comprising a reversible terminator comprises a non-optical label.

In some embodiments, nick labeling is performed using a labeled nucleotide comprising a reversible terminator. A single reversible-terminator-comprising labeled nucleotide can incorporated into a nick, so that no more than one label is incorporated into each nick. For example a linker connecting the nucleotide to the terminator can be cleaved. Following reversal of the terminator, the nick can be repaired. The label can then be detected, so as to detect a pattern of the first label on the DNA.

In some embodiments, labeling is carried out with a polymerase in the presence of at least one labeled dNTP using the process of nick translation. The labeled dNTP preferably contains a fluorophore or a quantum dot. In some embodiments, labeling is carried out as described in U.S. Provisional Application No. 61/713,862, which is hereby incorporated by reference in its entirety.

In some embodiments, the polymerase used herein leaves a flap region that is removed to generate a ligatable nick prior to repair. Without being limited by any one theory, the presence of one or more flap regions can interfere with ligation. Without being limited by any one theory, extension with a polymerase having 5' to 3' exonuclease activity can leave a flap region remaining, especially if the polymerase extension is performed under conditions with limited nucleotide concentrations. As such, in some embodiments, flap regions are removed following labeling that involves extension with a polymerase having 5' to 3' activity. In some preferred embodiments, repair is carried out with a DNA ligase. Examples of DNA ligases include Taq DNA ligase, *E. coli* DNA ligase, T7 DNA ligase, T4 DNA ligase, and 9° N DNA ligase (New England Biolabs). In some embodiments, the flap region is removed with an endonuclease. For example, in some preferred embodiments, the flap region is removed with a flap endonuclease (e.g., FEN I). In some embodiments, the flap region is removed with an exonuclease. In some preferred embodiments, the flap region is removed using the 5' to 3' exonuclease activity of a polymerase. In some preferred embodiments, the flap region is removed using the 5' to 3' exonuclease activity of a polymerase under conditions where at least one of four nucleotides (e.g., dATP, dGTP, dCTP, dTTP/dUTP) is provided in limited concentration. In some preferred embodiments, the flap region is removed using the 5' to 3' exonuclease activity of a polymerase under conditions where at least one of the four nucleotides is omitted. In some preferred embodiments, the flap region is removed using the 5' to 3' exonuclease activity of a Taq polymerase. In some embodiments, the flap is removed to restore ligatability of the translated nick. In some embodiments, the flap region is removed and the nick is repaired using a mixture of enzymes that perform these functions, such as PreCR enzyme mix (New England BioLabs). In some embodiments, the PreCR enzyme mix is used under conditions where at least one of the four nucleotides is provided in limited concentration or omitted.

Nucleotides that are not omitted during the flap removal process can be present at a concentration of about 25 nM to about 50 nM each, about 50 nM to about 100 nM, about 100 nM to about 200 nM, about 200 nM to about 400 nM, about 400 nM to about 800 nM, about 800 nM to about 1.6 uM, about 1.6 uM to about 3.2 uM, about 3.2 uM to about 6.4 uM, about 6.4 uM to about 12.8 uM, about 12.8 uM to about 25.6 uM, about 25.6 uM to about 51.2 uM, about 51.2 uM to about 102.4 uM, about 102.4 uM to about 204.8 uM, about 204.8 uM to about 409.6 uM, and about 409.6 uM to about 819.2 uM, about 819.2 uM to about 1638.4 uM, or about 1638.4 uM to about 3276.8 uM. In some preferred embodiments, the concentration of nucleotides that are not omitted is about 50 uM to about 500 uM each. In some preferred embodiments, the nucleotides that are present are present in equimolar amounts.

In some embodiments, the at least one nucleotide that is limited in concentration is at a concentration at least 2× less, at least 5× less, at least 10× less, at least 20λ, at least 30× less, at least 60× less, at least 100λ, at least 500× less, at least 1000× less, or at least 3000× less than at least one of the other nucleotides that is present. In some embodiments, the at least one nucleotide that is limited in concentration is at a concentration that is negligible compared to the nucleotides that are present. In some preferred embodiments, the at least one nucleotides that is limited in concentration is at a concentration at least 100× less that the nucleotides that are present.

In some embodiments, a method for repairing flap-containing DNA is provided. In some embodiments, at least one nucleotide is omitted prior to DNA characterization. For example, in some embodiments, the method entails treating a double stranded DNA containing at least one flap on either stand of the DNA with a 5' to 3' exonuclease activity of a polymerase under conditions wherein at least one nucleotide is omitted, ligating the nicks to restore strand integrity at the flap regions, and characterizing the DNA. In some embodiments, at least one nucleotide is limited in concentration prior to DNA characterization. For example, in some embodiments, the method entails treating a double stranded DNA comprising at least one flap on either stand of the DNA with a 5' to 3' exonuclease activity of a polymerase under conditions wherein at least one nucleotide is limited in concentration, ligating the nicks to restore strand integrity at the flap regions, and characterizing the DNA.

Methods for characterizing the molecules described herein include any method for determining the information content of the DNA, such as sequencing, mapping, single nucleotide polymorphism (SNP) analysis, copy number variant (CNV) analysis, haplotyping, or epigenetic analysis.

Unless defined otherwise, technical and scientific terms used herein have the same meaning as commonly understood by one of ordinary skill in the art.

The DNA described herein can be of any length (e.g., 0.1 Kb to a mega base). The DNA can be a highly pure preparation, crude, or semi-crude material. The DNA can come from any biological source or can be synthetic.

In some embodiments, two or more DNAs from the same biological source are analyzed. In some embodiments, two, three, four, five, six, seven, eight, nine, ten, or more DNAs from the same biological source are analyzed. In some embodiments, two or more DNAs from a single sample from biological source are analyzed, for example genomic DNA of a host organism. Optionally, DNAs from a source can be amplified prior to analysis. In some embodiments, the DNAs are analyzed simultaneously (in parallel). For example a first aliquot of a DNA from a source can be labeled in a first manner to produce a first pattern and a second aliquot of DNA from the same source can be labeled in a second manner to produce a second pattern. In some embodiments, at least two aliquots from the same sample are analyzed, for example two, three, four, five, six, seven, eight, nine, ten, or more aliquots. In some embodiments, the analysis is such that the multiple DNAs being analyzed are not in fluid communication with each other (e.g. each DNA can be in a separate aliquot). In some embodiments, one or both of the first pattern and second pattern are compared to one or more reference sequences. In some embodiments, the first pattern and second pattern are compared to each other.

In some embodiments, DNAs from two different biological sources are analyzed. In some embodiments, DNAs from different organisms are analyzed, and optionally compared. For example, two organisms of the same species can be compared to each other, or two organisms of related species can be compared to each other. In some embodiments, different DNAs from the same organisms are analyzed. For example a DNA from a first type of tissue or cell, can be compared to a DNA from a second type of tissue or cell. For example a DNA collected at a first timepoint or developmental stage can be compared to a DNA collected at a second timepoint or developmental stage.

As used herein, the term "polymerase" refers to any enzyme, naturally occurring or engineered, that is capable of incorporating native and modified nucleotides in a template dependent manner starting at a 3' hydroxyl end.

As used herein, the term "nicking endonuclease" refers to any enzyme, naturally occurring or engineered, that is capable of breaking a phosphodiester bond on a single DNA strand, leaving a 3'-hydroxyl at a defined sequence. Nicking endonucleases can be engineered by modifying restriction enzymes to eliminate cutting activity for one DNA strand, or produced by fusing a nicking subunit to a DNA binding domain, for example, zinc fingers and DNA recognition domains from transcription activator-like effectors.

Additional Alternative Embodiments

Methods for preparing samples and performing single molecule analysis, including methods of mitigating the effects of fragile sites and improving information density for genome mapping, are provided herein.

In an embodiment, a method of characterizing a DNA is provided, comprising: nicking a first DNA at a first sequence motif, wherein the first DNA is double stranded, and wherein the first DNA remains double-stranded adjacent to the nicks; labeling the nicks on the first DNA with a first label; repairing the nicks on the first DNA; marking the repaired first DNA with a second label, wherein the second label is non-sequence-specific, and wherein the second label is different from the first label; linearizing the first DNA following labeling with the first and second labels; and detecting the pattern of the first label on the linearized first DNA.

In an embodiment, a method of characterizing DNA is provided, comprising: nicking a first DNA at a first sequence motif, wherein the first DNA is double stranded, and wherein the first DNA remains double-stranded adjacent to the nicks; labeling the nicks on the first DNA with a first label; repairing the nicks on the first DNA following labeling with the first label; nicking the repaired first DNA at a second sequence motif, wherein the repaired first DNA remains double-stranded adjacent to the nicks; labeling the nicks at the second sequence motif on the first DNA with a second label; repairing the nicks on the first DNA following labeling with the second label; marking the first DNA with a third label, wherein the third label is non-sequence-specific, and wherein the third label is different from the first and second labels; linearizing the first DNA following labeling with the third label; detecting the pattern of at least one of the first and second labels on the first linearized DNA.

In an embodiment, a method of characterizing DNA is provided, comprising: nicking one strand of a first DNA at a recognition sequence with a first nicking endonuclease, wherein the first DNA is double stranded, and wherein the first DNA remains double-stranded adjacent to the nicks; labeling the first DNA at the nicking sites with a first label; repairing the nicks on the first DNA; nicking the complementary strand of a second DNA at the recognition sequence with a second nicking endonuclease, wherein the second DNA is double stranded, and wherein the second DNA remains double-stranded adjacent to the nicks; labeling the second DNA at the nicking sites with a second label; and repairing the nicks on the second DNA.

In some embodiments, the methods described herein further comprise: nicking one strand of a second DNA at a recognition sequence with the first nicking endonuclease, wherein the second DNA is double stranded, and wherein the second DNA remains double-stranded adjacent to the nicks; labeling the second DNA at the nicking sites repairing the nicks on the second DNA; nicking the complementary strand of the second DNA at the recognition sequence with the second nicking endonuclease; labeling the second DNA at the nicking sites; repairing the nicks on the second DNA; and marking the repaired first and second DNAs with a third label, wherein the third label is a non-sequence-specific label.

In an embodiment, a method of characterizing DNA is provided, comprising: nicking a first DNA at a first sequence motif, wherein the first DNA is double stranded, and wherein the first DNA remains double-stranded adjacent to the nicks; labeling the nicks on the first DNA with a first label; repairing the nicks on the first DNA; tagging the first DNA at a second sequence motif with a second label, wherein the second label does not cut DNA; marking the first DNA with a third label, wherein the third label is a non-sequence-specific label, and wherein the third label is different from the first and second labels; linearizing the first DNA following labeling with the first, second, and third labels; and detecting the first and second labels on the linearized first DNA.

In an embodiment, a method of characterizing DNA is provided, comprising: treating a double-stranded DNA comprising at least one flap on either strand of the DNA with a 5' to 3' exonuclease activity of a polymerase under conditions wherein at least one species of dNTP is in present in limited concentration compared to other dNTPs that are present; ligating the nicks to restore strand integrity at flap regions; and characterizing the DNA.

In an embodiment, a method of characterizing DNA is provided, comprising: treating a double-stranded DNA comprising at least one flap on either stand of the DNA with a 5' to 3' exonuclease activity of a polymerase under conditions wherein at least one species of dNTP is omitted; ligating the nicks to restore strand integrity at the flap regions; and characterizing the DNA.

In some embodiments, the methods described herein further comprise: nicking a second DNA at the first sequence motif; labeling the nicks on the second DNA with the first label; repairing the nicks on the second DNA; marking the repaired second DNA with the second label; linearizing the second DNA following labeling with the first and second labels; and detecting the pattern of the first or second label on the linearized second DNA.

In some embodiments, the methods described herein further comprise: nicking a second DNA at the first sequence motif, wherein the second DNA is double stranded, and wherein the second DNA remains double-stranded adjacent to the nicks; labeling the nicks on the second DNA with the first label; repairing the nicks on the second DNA following labeling with the first label; nicking the repaired second DNA at the second sequence motif, wherein the repaired second DNA remains double-stranded adjacent to the nicks; labeling the nicks at the second sequence motif on the second DNA with the second label; repairing the nicks on the second DNA following labeling with the second label; marking the second DNA with the third label; linearizing the second DNA following labeling with the third label; and detecting the pattern of at least one of the first and second labels on the second linearized DNA.

In some embodiments, the methods described herein further comprise comparing the pattern of the first label on the first DNA to the pattern of the first label on the second DNA. In some embodiments, the methods described herein further comprise: assembling a plurality of first DNAs using overlap of the labeled sequence motifs to construct a first DNA map; assembling a plurality of second DNAs using overlap of the labeled sequence motifs to construct a second DNA map; and comparing the first DNA map to the second DNA map.

In some embodiments, the methods described herein further comprise: marking the repaired first and second DNAs with a third label, wherein the third label is a non-sequence-specific label. In some embodiments, the methods described herein further comprise: linearizing the first and second DNAs; detecting the first and second labels on the linearized DNA; and assembling the labeled DNA molecules using overlap of the labeled sequence motifs to construct a DNA map. In some embodiments, the first and second labels are the same label. In some embodiments, the first and second labels comprise different labels.

In some embodiments, the methods described herein further comprise: nicking a second DNA at the first sequence motif, wherein the second DNA is double stranded, and wherein the second DNA remains double-stranded adjacent to the nicks; labeling the nicks on the second DNA with the first label; repairing the nicks on the second DNA; tagging the second DNA at the second motif with the second label; marking the second DNA with the third label; linearizing the second DNA following labeling with the first and second labels; and detecting the first and second labels on the linearized second DNA.

In some embodiments, the linearizing includes transporting the DNA into a nanochannel. In some embodiments, the methods described herein further comprise comparing the pattern of at least one of the first or second labels on the first DNA to a pattern of labels on a reference DNA. In some embodiments, the methods described herein further comprise comparing the pattern of the first label on the first DNA to a pattern of labels on a reference DNA. In some embodiments, the methods described herein further comprise comparing the pattern of the second label on the first DNA to a pattern of labels on a reference DNA, wherein the second label is a sequence specific label. In some embodiments, the methods described herein further comprise assembling the labeled first DNA using the pattern of labeled motifs to construct a first DNA map. In some embodiments, the methods described herein further comprise assembling the labeled second DNA using the pattern of labeled motifs to construct a first DNA map. In some embodiments, the second label is a non-sequence-specific label. In some embodiments, the second sequence motif includes at least one binding site for a DNA binding entity selected form the group consisting of a non-cutting restriction enzyme, a zinc finger protein, an antibody, a transcription factor, a transcription activator like domain, a DNA binding protein, a polyamide, a triple helix forming oligonucleotide, and a peptide nucleic acid, wherein the tagging is effected with the binding entity comprising the second label, and wherein the second label is selected form the group consisting of a fluorophore, a quantum dot, a dendrimer, a nanowire, a bead, a hapten, streptavidin, avidin, neutravidin, biotin, and a stabilized reactive group. In some embodiments, the second sequence motif includes at least one binding site for a peptide nucleic acid, wherein the tagging is performed with the peptide nucleic acid comprising the second label, and wherein the second label is a fluorophore or a quantum dot. In some embodiments, the second sequence motif includes at least one binding site for a methyltransferase, and wherein tagging is performed with the methyltransferase comprising a modified cofactor which includes the second label. In some embodiments, the first and second labels are independently selected from the group consisting of a fluorophore, a quantum dot, a dendrimer, a nanowire, a bead, a hapten, a streptavidin, an avidin, a neutravidin, a biotin, a reactive group, and a non-optical label. In some embodiments, the first and second labels are independently selected from the group consisting of a fluorophore or a quantum dot. In some embodiments, the labeling is carried out with a polymerase. In some embodiments, the labeling is carried out with a polymerase in the presence of dNTPs comprising the label. In some embodiments, the polymerase has a 5' to 3' exonuclease activity. In some embodiments, the polymerase leaves a flap region, and wherein the flap region is removed to restore a ligatable nick prior to the repairing with a ligase. In some embodiments, the flap region is removed using the 5' to 3' exonuclease activity of a polymerase under conditions wherein at least one nucleotide is present in limited concentration. In some embodiments, the flap region is removed using the 5' to 3' exonuclease activity of a polymerase under conditions wherein at least one nucleotide is omitted from the reaction. In some embodiments, the flap region is removed with a flap endonuclease. In some embodiments, the labeling is carried out with a polymerase in the presence of at least one species of dNTP. In some embodiments, the at least one species of dNTP is a single species of dNTP. In some embodiments, activity of the polymerase is modulated by adjusting the temperature, dNTP concentration, cofactor concentration, buffer concentration, or any combination thereof, during labeling.

EXAMPLES

The following examples are intended to illustrate, but not to limit, the invention in any manner, shape, or form, either explicitly or implicitly. While they are typical of those that might be used, other procedures, methodologies, or techniques known to those skilled in the art may alternatively be used.

Example 1

E. coli genomic DNA was nicked with Nt.BspQI nicking endonuclease. The nicked DNA was labeled with Taq polymerase by nick translation using Atto dUTP or Alexa dUTP in the presence of cold dATP, dGTP, and dCTP. The labeled nicks were: 1.) not repaired, 2.) repaired with PreCR as recommended by manufacture (New England BioLabs), 3.) repaired with PreCR under conditions of omitting dGTP, 4.) repaired with PreCR under conditions of omitting dATP and dGTP, or 5.) repaired with Taq polymerase under conditions of omitting dGTP. Ligation was then performed with a ligase. The resulting DNA was stained with YOYO-1 (Life Technologies) and processed on the Irys system (BioNano Genomics). Briefly, DNA was linearized in massively parallel nanochannels, excited with the appropriate laser for backbone and label detection, and optically imaged. Mapping to a reference genome, center of mass, and False Positive (FP) and False Negative (FN) calculations were carried out using nanoStudio data analysis software (BioNano Genomics). Results are shown in FIG. 2.

Example 2

E. coli genomic DNA was nicked with Nt.BspQI nicking endonuclease. The nicked DNA was labeled with Taq polymerase by nick translation using Atto dUTP. The labeled DNA was: 1.) left unrepaired or 2.) treated with FEN I to remove flaps followed by a ligase to repair the translated nicks. The DNA was linearized in massively parallel nanochannels, excited with the appropriate laser for backbone and label detection, and optically imaged. Mapping to a reference genome, center of mass, and False Positive (FP) and False Negative (FN) calculations were carried out using nanoStudio data analysis software (BioNano Genomics). Results are shown in FIG. 3.

Example 3

Drosophila genomic DNA was nicked with Nt.BspQI or Nb.BbVCI nicking endonuclease. The nicked DNA was labeled with Taq polymerase by nick translation using Atto dUTP. The labeled DNA was treated with PReCR reagent (New England Biolabs) to repair the nicks. The resulting DNA was stained with YOYO-1 (Life Technologies) and processed on the Irys system (BioNano Genomics). Mapping to a reference genome, center of mass, and False Positive (FP) and False Negative (FN) calculations were carried out using nanoStudio data analysis software (BioNano Genomics). Results are shown in FIG. 4.

Example 4

A genome map was constructed using two nicking enzymes, Nt.BbvCI and Nt.BspQI, whose nick motifs were labeled with red and green dyes, respectively, across 27 BACs making up an MTP of a 2.1-Mb region containing the prolamin multigene family in the *Ae. tauschii* genome. FIG. 5A shows the layout of the IrysChip (BioNano Genomics).

Figure 5B:
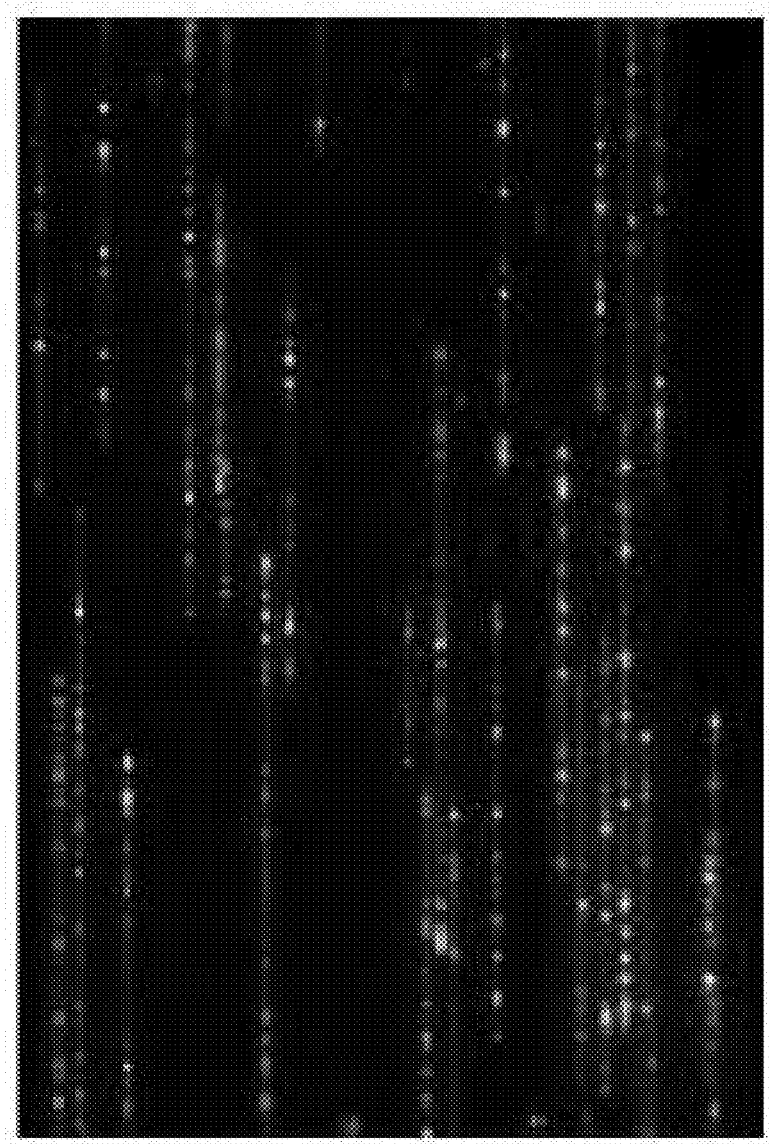
Figure 5C:
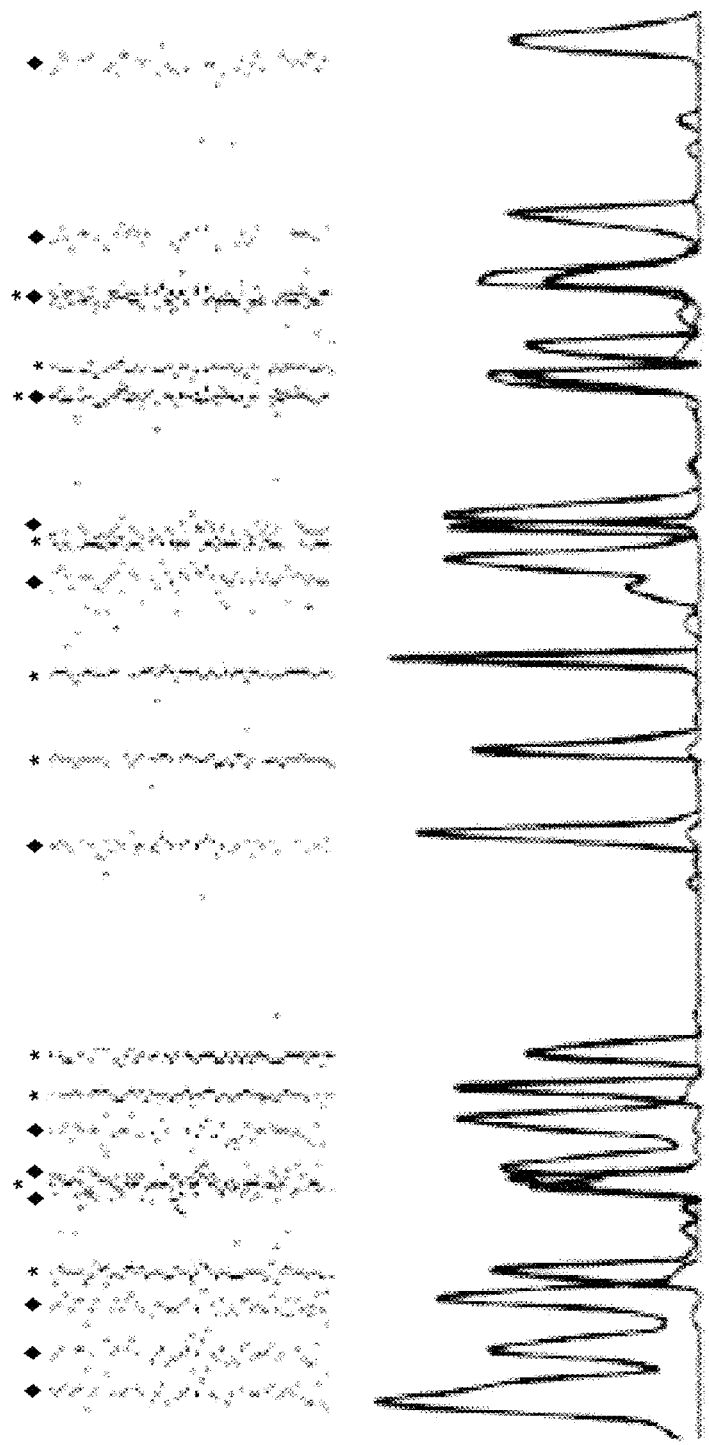
Figure 5D:
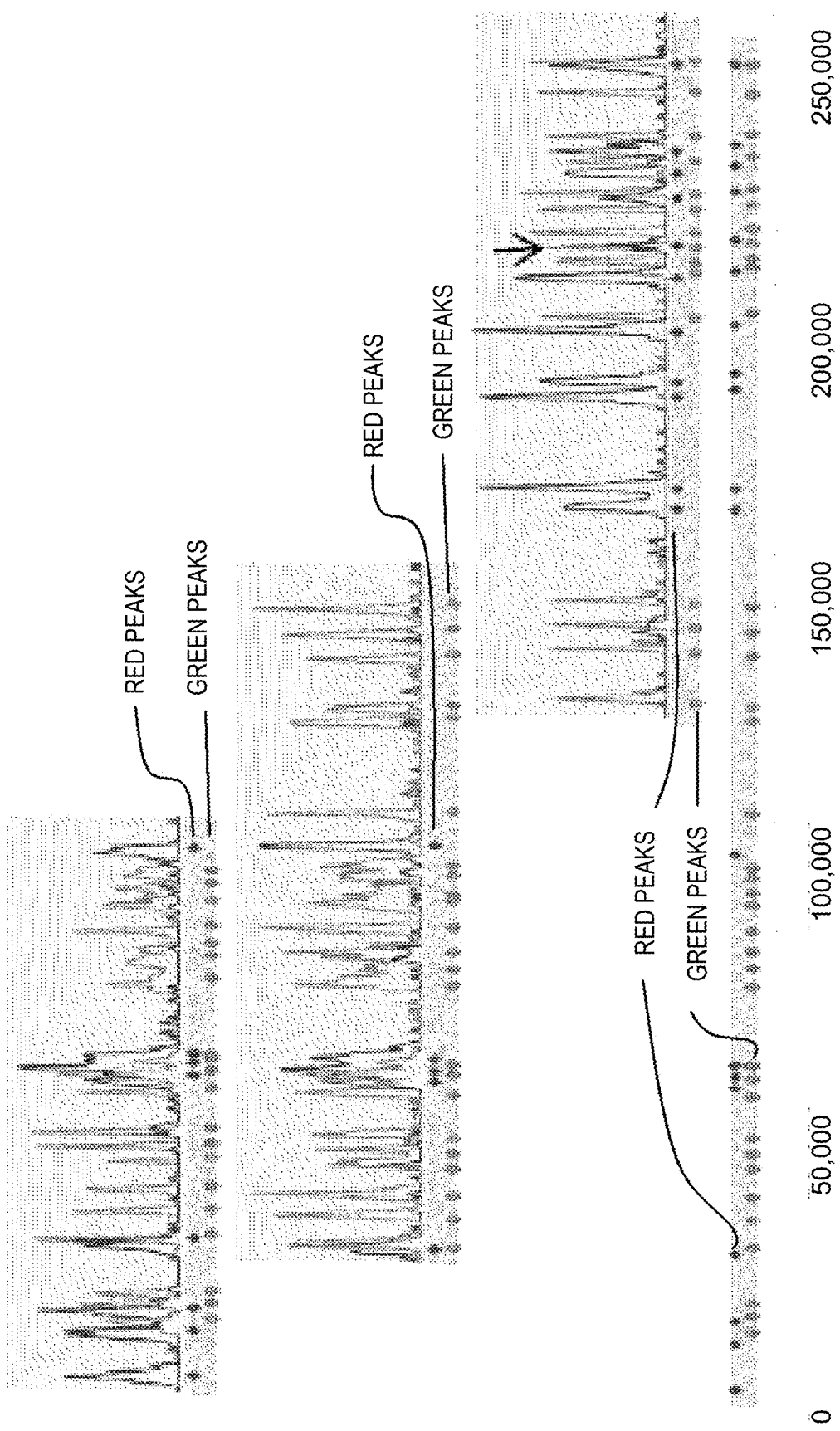
Figure 5E:
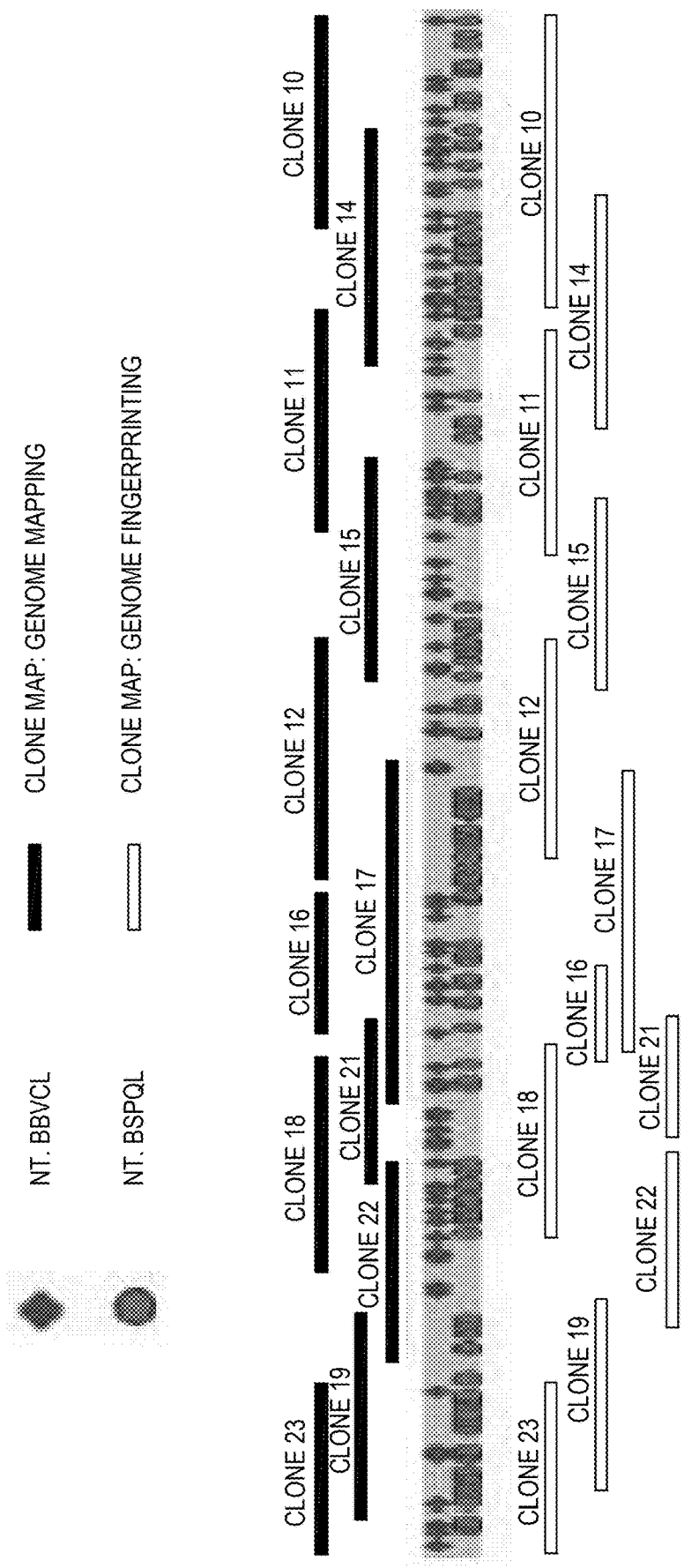
Figure 5F:
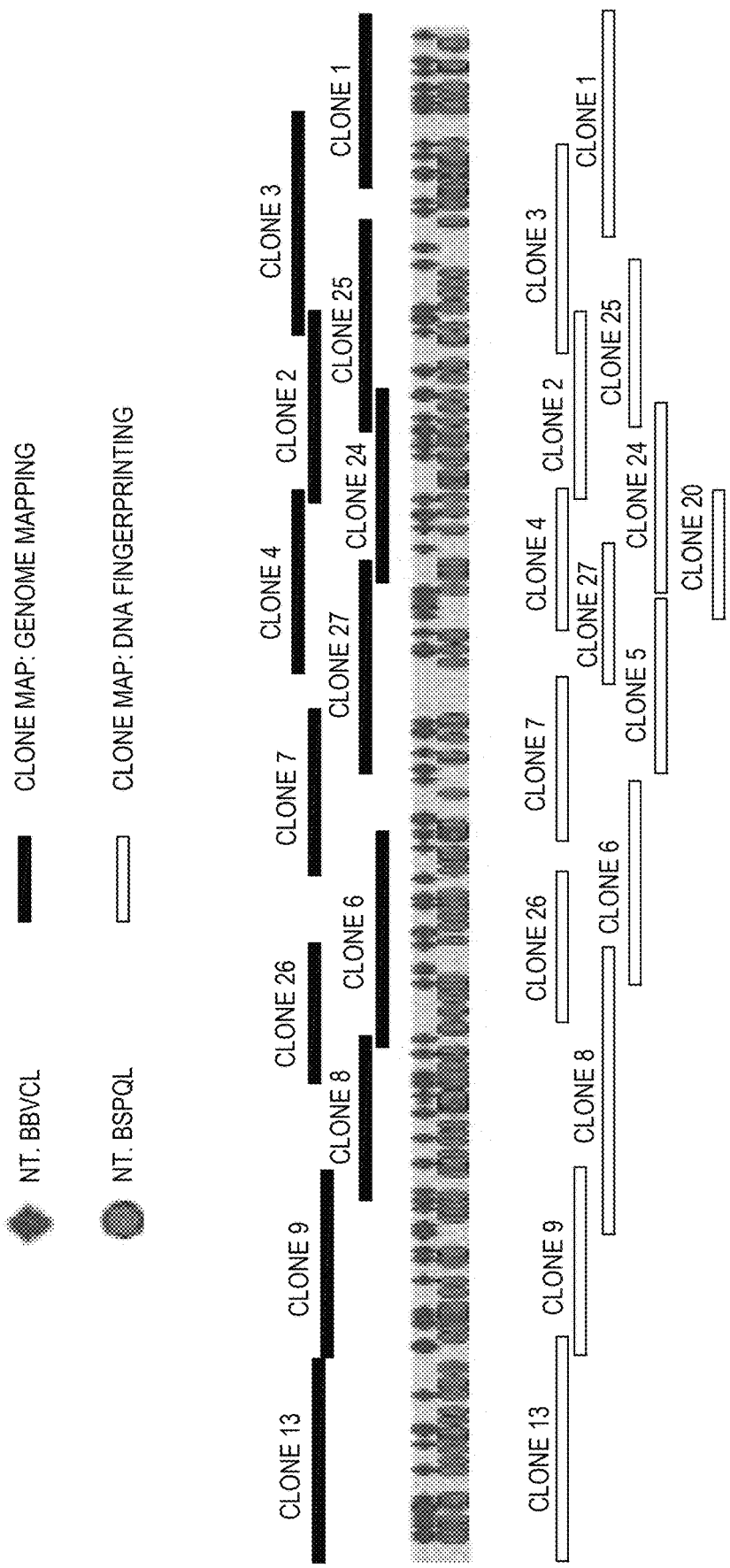

The YOYO-stained DNA was loaded into the port, unwound within the pillar structures, and linearized inside 45 nm nanochannels (FIG. 5B). After image processing, individual BAC molecules with red and green labels distributed at sequence-specific locations were compared and clustered into pools with similar map patterns (FIG. 5C, top). In FIG. 5C, positions of green labeling are indicated by a diamond (♦) and positions of red labeling are indicated by a asterisk (*). Density plots for the BAC clones were generated to determine the consensus peak locations (FIG. 5C, bottom). The consensus maps of individual BAC clones were aligned based on overlaps of consensus maps of adjacent BACs (FIG. 5D) to create a genome map of the entire region. In FIG. 5D, peak colors are summarized by symbols displayed beneath the line graph, such that red peaks are indicated by a symbol in the upper row, and green peaks are indicated by a symbol in the lower row. An exemplary map of the genomic region based on overlaps of consensus maps is illustrated in FIG. 5E.

The two-color labeling strategy resulted in an average information density of one label per 4.8 kb (437 labels in 2.1 Mb). Since each motif was marked by its own color, peaks of different motifs could be distinguished from each other even if their peaks were almost overlapping (arrow in FIG. 5D). Peaks of the same motif (i.e., the same color) could be resolved when they were at least ~1.5 kb apart. Taking advantage of the combination of long molecule lengths (~140 kb average), high-resolution, accurate length measurement, and multiple sequence motifs, a high-quality genome map of the 2.1-Mb region for scaffold assembly was generated.

REFERENCES

1. Blakesley R, Hansen N, Gupta J, McDowell J, Maskeri B, et al. (2010) Effort required to finish shotgun-generated genome sequences differs significantly among vertebrates. BMC Genomics 11: 21.
2. Chain P S G, Grafham D V, Fulton R S, FitzGerald M G, Hostetler J, et al. (2009) Genome Project Standards in a New Era of Sequencing. Science 326: 236-237.
3. Lee H, Tang H (2012) Next-generation sequencing technologies and fragment assembly algorithms. Methods Mol Biol 855: 155-174.
4. Green E D (2001) Strategies for the systematic sequencing of complex genomes. Nat Rev Genet 2: 573-583.
5. McPherson TIHGMCJD (2001) A physical map of the human genome. Nature 409: 934-941.
6. Smith D B, Flavell R B (1975) Characterisation of the wheat genome by renaturation kinetics. Chromosoma 50: 223-242.
7. Venter J C, Adams M D, Myers E W, Li P W, Mural R J, et al. (2001) The Sequence of the Human Genome. Science 291: 1304-1351.
8. Zuccolo A, Sebastian A, Talag J, Yu Y, Kim H, et al. (2007) Transposable element distribution, abundance and role in genome size variation in the genus *Oryza*. BMC Evolutionary Biology 7: 152.
9. Initiative TAG (2000) Analysis of the genome sequence of the flowering plant *Arabidopsis thaliana*. Nature 408: 796-815.
10. Project IRGS (2005) The map-based sequence of the rice genome. Nature 436: 793-800.
11. Zhou S, Wei F, Nguyen J, Bechner M, Potamousis K, et al. (2009) A single molecule scaffold for the maize genome. PLoS Genet 5: e1000711.
12. Schnable P S, Ware D, Fulton R S, Stein J C, Wei F, et al. (2009) The B73 maize genome: complexity, diversity, and dynamics. Science 326: 1112-1115.
13. Luo M C, Thomas C, You F M, Hsiao J, Ouyang S, et al. (2003) High-throughput fingerprinting of bacterial artificial chromosomes using the snapshot labeling kit and sizing of restriction fragments by capillary electrophoresis. Genomics 82: 378-389.
14. Paux E, Sourdille P, Salse Jrm, Saintenac C, Choulet Fdr, et al. (2008) A Physical Map of the 1-Gigabase Bread Wheat Chromosome 3B. Science 322: 101-104.
15. Philippe R, Choulet F, Paux E, van Oeveren J, Tang J, et al. (2012) Whole Genome Profiling provides a robust framework for physical mapping and sequencing in the highly complex and repetitive wheat genome. BMC Genomics 13: 47.
16. van Oeveren J, de Ruiter M, Jesse T, van der Poel H, Tang J, et al. (2011) Sequence-based physical mapping of complex genomes by whole genome profiling. Genome Research 21(4): 618-625.
17. Schwartz D C, Li X, Hernandez L I, Ramnarain S P, Huff E J, et al. (1993) Ordered restriction maps of *Saccharomyces cerevisiae* chromosomes constructed by optical mapping. Science 262: 110-114.
18. Teague B, Waterman M S, Goldstein S, Potamousis K, Zhou S, et al. (2010) High-resolution human genome structure by single-molecule analysis. Proc Natl Acad Sci USA 107: 10848-10853.
19. Lam E T, Hastie A, Lin C, Ehrlich D, Das S K, et al. (2012) Genome mapping on nanochannel arrays for structural variation analysis and sequence assembly. Nat Biotechnol 30: 771-776.
20. Mun J H, Kwon S J, Yang T J, Kim H S, Choi B S, et al. (2008) The first generation of a BAC-based physical map of *Brassica rapa*. BMC Genomics 9: 280.
21. Zhou S, Bechner M C, Place M, Churas C P, Pape L, et al. (2007) Validation of rice genome sequence by optical mapping. BMC Genomics 8: 278.
22. Nagarajan N, Read T D, Pop M (2008) Scaffolding and validation of bacterial genome assemblies using optical restriction maps. Bioinformatics 24: 1229-1235.
23. Howden B P, Seemann T, Harrison P F, McEvoy C R, Stanton J A, et al. (2010) Complete genome sequence of *Staphylococcus aureus* strain JKD6008, an ST239 clone of methicillin-resistant *Staphylococcus aureus* with intermediate-level vancomycin resistance. J Bacteriol 192: 5848-5849.
24. Riley M C, Lee J E, Lesho E, Kirkup B C, Jr. (2011) Optically mapping multiple bacterial genomes simultaneously in a single run. PLoS One 6: e27085.
25. Lin H C, Goldstein S, Mendelowitz L, Zhou S, Wetzel J, et al. (2012) AGORA: Assembly Guided by Optical Restriction Alignment. BMC Bioinformatics 13: 189.
26. Xiao M, Phong A, Ha C, Chan T-F, Cai D, et al. (2007) Rapid DNA mapping by fluorescent single molecule detection. Nucleic Acids Research 35: e16.
27. Das S K, Austin M D, Akana M C, Deshpande P, Cao H, et al. (2010) Single molecule linear analysis of DNA in nano-channel labeled with sequence specific fluorescent probes. Nucleic Acids Research 38: e177.
28. Dvorak J (2009) Triticeae Genome Structure and Evolution. Genetics and Genomics of the Triticeae Springer Science.

29. Li W, Zhang P, Fellers J P, Friebe B, Gill B S (2004) Sequence composition, organization, and evolution of the core Triticeae genome. Plant J 40: 500-511.
30. Cassidy B G, Dvorak J (1991) Molecular Characterization of a Low-Molecular-Weight Glutenin Cdna Clone from Triticum-Durum. Theoretical and Applied Genetics 81: 653-660.
31. Hernandez P, Martis M, Dorado G, Pfeifer M, Galvez S, et al. (2012) Next-generation sequencing and syntenic integration of flow-sorted arms of wheat chromosome 4A exposes the chromosome structure and gene content. Plant J 69: 377-386.
32. Leroy P, Guilhot N, Sakai H, Bernard A, Choulet F, et al. (2012) TriAnnot: A Versatile and High Performance Pipeline for the Automated Annotation of Plant Genomes. Front Plant Sci 3: 5.
33. Brenchley R, Spannagl M, Pfeifer M, Barker G L, D'Amore R, et al. (2012) Analysis of the bread wheat genome using whole-genome shotgun sequencing. Nature 491: 705-710.
34. Li Y, Zheng H, Luo R, Wu H, Zhu H, et al. (2011) Structural variation in two human genomes mapped at single-nucleotide resolution by whole genome de novo assembly. Nat Biotechnol 29: 723-730.
35. Soderlund C, Longden I, Mott R (1997) FPC: a system for building contigs from restriction fingerprinted clones. Comput Appl Biosci 13: 523-535.
36. Warren R L, Varabei D, Platt D, Huang X, Messina D, et al. (2006) Physical map-assisted whole-genome shotgun sequence assemblies. Genome Res 16: 768-775.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims. One skilled in the art will appreciate that, for this and other processes and methods disclosed herein, the functions performed in the processes and methods can be implemented in differing order. Furthermore, the outlined steps and operations are only provided as examples, and some of the steps and operations can be optional, combined into fewer steps and operations, or expanded into additional steps and operations without detracting from the essence of the disclosed embodiments.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

What is claimed:

1. A method of analyzing a double-stranded DNA, the method comprising:
    nicking a top strand of the double-stranded DNA at a first sequence motif with a first nickase, thereby generating a first site of nicking in the top strand;
    nicking a bottom strand of the double-stranded DNA with a second nickase that recognizes the same sequence motif as the first nickase, thereby generating a second site of nicking in the bottom strand, wherein the DNA remains double-stranded adjacent to the nicks;
    wherein the first site of nicking in the top strand and the second site of nicking in the bottom strand are less than 1 kb apart,
    labeling the first and second sites of nicking with a first label, wherein the labeling comprises nick translation, wherein the labeling is carried out with a polymerase that leaves a flap region,
    wherein said nick translation comprises extension in a direction from the first site of nicking on the top strand, and extension in an opposite direction from the second site of nicking on the bottom strand, by which a distance between the first and second nick sites increases, thereby stabilizing the double-stranded DNA;
    repairing the nicks on the double-stranded DNA, wherein the repairing is carried out by a ligase, and wherein the flap region is removed to restore a ligatable nick prior to the repairing with a ligase;
    nicking the repaired double-stranded DNA at a second sequence motif, wherein the repaired double-stranded DNA remains double-stranded adjacent to the nicks;
    labeling the nicks at the second sequence motif on the double-stranded DNA with a second label;
    repairing the nicks on the double-stranded DNA following labeling with the second label;
    transporting the repaired and labeled double-stranded DNA into a nanochannel having a width of 1 nanometer to 500 nanometers and a depth of 1 nanometer to 500 nanometers;
    detecting the pattern of the first label and the pattern of the second label on the double-stranded DNA in the nanochannel; and
    constructing a DNA map of the double-stranded DNA, the DNA map comprising the pattern of the first label and the pattern of the second label on the double-stranded DNA in the nanochannel.

2. The method of claim 1, further comprising marking the double-stranded DNA with a third label, wherein the third label is non-sequence-specific, and wherein the third label is different from the first label, and wherein the third label is different from the second label.

3. The method of claim 1, further comprising modulating activity of a polymerase by adjusting the temperature, dNTP concentration, cofactor concentration, buffer concentration, or any combination thereof, during labeling.

4. The method of claim 1, wherein the labeling is carried out in the presence of labeled dNTPs, and wherein the polymerase has a 5' to 3' exonuclease activity, wherein the 5' to 3' exonuclease activity is performed under conditions in which at least one nucleotide is omitted, thereby removing the flap region and restoring a ligatable nick.

5. The method of claim 1, further comprising comparing the pattern of the first label on the double-stranded DNA to a pattern of labels on a reference DNA.

6. The method of claim 1, wherein:
    the first nickase is Nb.BbvCI and the second nickase is Nt.BbvCI; or
    the first nickase is Nt.BbvCI and the second nickase is Nb.BbvCI.

7. The method of claim 1, wherein the flap region is removed with a flap endonuclease.

8. The method of claim 1, wherein the DNA map is a physical map of the double-stranded DNA.

9. The method of claim 1, wherein the first label comprises Atto dUTP or Alexa dUTP.

10. The method of claim 9, wherein the labeling is carried out in the presence of dATP, dGTP, and dCTP.

11. A method of analyzing a DNA comprising:
    nicking one strand of a first DNA with a first nicking endonuclease at a recognition sequence, thereby generating a first nicking site, wherein the first DNA remains double-stranded adjacent to the first nicking site;
    labeling the first DNA at the first nicking site with a first label;
    repairing the first nicking site on the first DNA;
    nicking a complementary strand of a second DNA at the recognition sequence with a second nicking endonuclease, thereby generating a second nicking site, wherein the complementary strand of the second DNA is complementary to the one strand of the first DNA, wherein the second DNA is double stranded, wherein the second nicking endonuclease recognizes the same sequence motif as the first nicking endonuclease, and wherein the second DNA remains double-stranded adjacent to the second nicking site;
    labeling the second DNA at the second nicking site with a second label, wherein the labeling is carried out with a polymerase that leaves a flap region; and wherein the first label and the second label are different;
    repairing the second nicking site on the second DNA, wherein the repairing is carried out by a ligase, and wherein the flap region is removed to restore a ligatable nick prior to the repairing with a ligase;
    transporting the repaired first DNA and the repaired second DNA into a nanochannel having a width of 1 nanometer to 500 nanometers and a depth of 1 nanometer to 500 nanometers;
    detecting a pattern of the first label on the first DNA and a pattern of the second label on the second DNA in the nanochannel;
    constructing a DNA map of the second DNA, the DNA map comprising the pattern of the second label on the double-stranded DNA in the nanochannel.

12. The method of claim 11, further comprising marking the repaired first and second DNA with a third label, wherein the third label is non-sequence specific.

13. The method of claim 11, wherein:
    the first nicking endonuclease is Nb.BbvCI and the second nicking endonuclease is Nt.BbvCI; or
    the first nicking endonuclease is Nt.BbvCI and the second nicking endonuclease is Nb.BbvCI.

14. The method of claim 11, wherein the flap region is removed with a flap endonuclease.

15. The method of claim 11, wherein the polymerase has a 5' to 3' exonuclease activity, and wherein the flap region is removed using the 5' to 3' exonuclease activity of the polymerase under conditions in which at least one nucleotide is limited or omitted.

16. The method of claim 15, wherein the limited at least one nucleotide is in a concentration at least 100× less than at least one of the other nucleotides that is present.

* * * * *